United States Patent
Tawa et al.

(10) Patent No.: US 10,058,281 B2
(45) Date of Patent: Aug. 28, 2018

(54) ACTIVITY AMOUNT-RELATED INFORMATION DISPLAY APPARATUS

(71) Applicant: OMRON HEALTHCARE CO., LTD., Muko-shi, Kyoto (JP)

(72) Inventors: Yasuhisa Tawa, Kyoto (JP); Yuzuki Tamai, Kyoto (JP); Shusuke Eshita, Kyoto (JP); Tsuyoshi Ogihara, Kyoto (JP); Tamaki Ito, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 87 days.

(21) Appl. No.: 15/189,179

(22) Filed: Jun. 22, 2016

(65) Prior Publication Data

US 2016/0302717 A1    Oct. 20, 2016

Related U.S. Application Data

(63) Continuation of application No. PCT/JP2014/082959, filed on Dec. 12, 2014.

(30) Foreign Application Priority Data

Dec. 26, 2013  (JP) ................................. 2013-269843

(51) Int. Cl.
*A61B 5/11*    (2006.01)
*G06T 1/00*    (2006.01)
(Continued)

(52) U.S. Cl.
CPC ............ *A61B 5/486* (2013.01); *A61B 5/1118* (2013.01); *A61B 5/4866* (2013.01); *A61B 5/742* (2013.01);
(Continued)

(58) Field of Classification Search
CPC combination set(s) only.
See application file for complete search history.

(56) References Cited

U.S. PATENT DOCUMENTS 6,429,869 B1 *  8/2002  Kamakura .......... G06F 3/04847
                                                      345/440
8,004,527 B2 *  8/2011  Culpi .................... G06T 11/206
                                                      324/103 R
(Continued)

FOREIGN PATENT DOCUMENTS

CN    101219046 A    7/2008
CN    102743153 A    10/2012
(Continued)

OTHER PUBLICATIONS

Official Communication issued in International Patent Application No. PCT/JP2014/082959, dated Feb. 24, 2015.

*Primary Examiner* — Wesner Sajous
(74) *Attorney, Agent, or Firm* — Keating and Bennett, LLP

(57) ABSTRACT

An activity amount-related information display apparatus according to the present invention acquires value information indicating exercise intensity, activity amount, or expended calories of a measurement subject. On a display screen, a circle corresponding to one day is set, and time divisions each indicating elapse of a unit time in the one day are set clockwise around the circle. Value information is displayed as a graph composed of a collection of bars that extend outward in a radial direction around the circle and have lengths of multiple levels, the lengths each corresponding to a value indicated by the value information for a unit time.

7 Claims, 10 Drawing Sheets

(51) Int. Cl.
*G06T 11/00* (2006.01)
*G06T 11/20* (2006.01)
*A61B 5/00* (2006.01)
*G06F 19/00* (2018.01)
*G16H 15/00* (2018.01)

(52) U.S. Cl.
CPC .......... *G06F 19/00* (2013.01); *G06F 19/3481* (2013.01); *G06T 1/0007* (2013.01); *G06T 11/001* (2013.01); *G06T 11/206* (2013.01); *G16H 15/00* (2018.01); *A61B 5/6823* (2013.01); *A61B 5/6838* (2013.01); *A61B 2562/0219* (2013.01); *G06T 2210/41* (2013.01)

(56) References Cited

U.S. PATENT DOCUMENTS

| | | | |
|---|---|---|---|
| 8,914,740 B1* | 12/2014 | Joos | G06F 3/048 345/440 |
| 9,041,716 B2* | 5/2015 | Ogles | G05B 19/409 345/440 |
| 9,126,088 B2* | 9/2015 | Asada | A61B 5/1118 |
| 2007/0176933 A1 | 8/2007 | Culpi et al. | |
| 2013/0106684 A1* | 5/2013 | Weast | G06F 19/3481 345/156 |
| 2013/0222392 A1* | 8/2013 | Ogles | G05B 19/409 345/440.2 |
| 2014/0266731 A1* | 9/2014 | Malhotra | G06F 1/163 340/573.1 |
| 2017/0259116 A1* | 9/2017 | Mestas | A63B 24/0062 |

FOREIGN PATENT DOCUMENTS

| | | |
|---|---|---|
| JP | 8-308820 A | 11/1996 |
| JP | 2008-167937 A | 7/2008 |
| JP | 2009-530632 A | 8/2009 |
| JP | 2013-215347 A | 10/2013 |

* cited by examiner

EXERCISE INTENSITY [METs]

ACTIVITY AMOUNT-RELATED INFORMATION DISPLAY APPARATUS

BACKGROUND OF THE INVENTION

1. Field of the Invention

The present invention relates to an activity amount-related information display apparatus, and more specifically relates to an activity amount-related information display apparatus that displays information relating to an activity amount of a measurement subject as a graph on a display screen.

In the present specification, "information relating to an activity amount" includes at least:

i) exercise intensity (unit: [METs], which is an abbreviation for "metabolic equivalents", an amount expressing the ratio of the exercise intensity with respect to the exercise intensity during a resting time);

ii) activity amount (unit: [Ex], which is an amount obtained by multiplying the exercise intensity [METs] by the amount of time (unit: [h]; hours) for which the exercise was performed; i.e., [Ex]=[METs·h]);

iii) expended calories (unit: [kcal], which is obtained by multiplying the activity amount [Ex] by the body weight [kg] of the body; i.e., expended calories [kcal]=activity amount [Ex]×body weight [kg]); and iv) achievement degrees with respect to target values for the values of i) to iii) above (collectively referred to as "target value relating to activity amount" as appropriate).

2. Description of the Related Art

Conventionally, as this type of activity amount-related information display apparatus, there has been an activity amount-related information display apparatus such as that described in Panasonic Corporation, "Product Advantages of Activity Meter EW-NK63", [online], [searched for on 11/25/2013], Internet <URL: http://panasonic.jp/calorimeter/day-calorie/ew_nk63/recommend/>, for example, in which daily expended calories over one week, for example, of the measurement subject are displayed as a bar graph on a smartphone display screen with a time axis indicating days, weeks, months, or the like on the horizontal axis and with the expended calories (unit: [kcal]) on the vertical axis.

SUMMARY OF THE INVENTION

However, with the above-described conventional display method, there is a problem in that information relating to the activity amount for each unit time in one day of a measurement subject is difficult for a user (includes the measurement subject; the same follows below) to understand intuitively. Also, there is a problem in that the achievement degree with respect to a target value relating to an activity amount of the measurement subject is difficult for a user to understand intuitively.

In view of this, it is an object of the present invention to provide an activity amount-related information display apparatus that can display information relating to the activity amounts of a measurement subject for each unit time in one day on a display screen such that it is easy to understand intuitively. It is also an object of the present invention to provide an activity amount-related information display apparatus that can display an achievement degree with respect to a target value relating to an activity amount of a measurement subject on a display screen such that it is easy to understand intuitively.

In order to solve the foregoing problems, an activity amount-related information display apparatus according to the present invention is an activity amount-related information display apparatus for displaying information relating to an activity amount of a measurement subject as a graph on a display screen, including:

a value information acquisition unit configured to acquire value information indicating an exercise intensity, an activity amount, or expended calories of the measurement subject; and a first display processing unit configured to, on the display screen, set a circle or a circular arc corresponding to one day, set time divisions each indicating elapse of a unit time in the one day clockwise around the circle or the circular arc, and display the value information as a graph composed of a collection of bars that extend outward in a radial direction around the circle or the circular arc and have lengths of a plurality of levels, the lengths each corresponding to a value indicated by the value information for a unit time.

With the activity amount-related information display apparatus according to the present invention, the value information acquisition unit acquires the value information indicating the exercise intensity, activity amount, or expended calories of the measurement subject. On the display screen, the first display processing unit sets a circle or a circular arc corresponding to one day, sets time divisions each indicating elapse of a unit time in the one day clockwise around the circle or circular arc, and displays the value information as a graph composed of a collection of bars that extend outward in a radial direction around the circle or circular arc and have lengths of multiple levels, the lengths each corresponding to a value indicated by the value information for a unit time. For example, if the value indicated by the value information is small as a result of the measurement subject performing weak exercise for a certain unit time, a short bar will be displayed. On the other hand, if the value indicated by the value information is large as a result of the measurement subject performing vigorous exercise for another unit time, a long bar will be displayed. Accordingly, the user can intuitively know the exercise intensity, activity amount, or expended calories for each unit time as information relating to the activity amount for each unit time in one day of the measurement subject.

In particular, if the first display processing unit sets a circle (not a circular arc) corresponding to one day on the display screen, the time divisions look like the divisions of an analog 24-hour clock. Accordingly, the user can intuitively know that the information relating to the activity amount displayed on the display screen is one day's-worth of information.

With an activity amount-related information display apparatus according to an embodiment, the first display processing unit divides the bars into segments for each of the levels in the radial direction, and colors the segments with colors with higher color temperatures the higher the levels are.

With the activity amount-related information display apparatus according to the embodiment, the first display processing unit divides the bars into segments for each of the levels in the radial direction, and colors the segments with colors having higher color temperatures the higher the levels are. That is, if the value indicated by the value information is small as a result of the measurement subject performing weak exercise for a certain unit time, the length of the bar will be small, there will be a small number of segments, and all of the segments will be colored with colors having low color temperatures. On the other hand, if the value indicated by the value information is large as a result of the measurement subject performing vigorous exercise for another unit time, the length of the bar will be long, there will be a higher number of segments, and high-level segments will be colored with colors having high color temperatures. The "color temperature" in this context suggests to the user the exercise intensity or the degree of energy expenditure due to exercise of the measurement subject. Accordingly, the user can more intuitively know the exercise intensity, activity amount, or expended calories for each unit time of the measurement subject.

A first-level segment, which is the lowest of the segments of the plurality of levels, or a first-level segment and a subsequent second-level segment may be colored green. This is because green is associated with a calm state in which the exercise intensity, activity amount, or expended calories are relatively low. In such a case, only the segments with higher levels than the green-colored segments may be colored with colors having higher color temperatures the higher the levels are.

With an activity amount-related information display apparatus according to an embodiment, on the display screen, the first display processing unit grays out a graph for a previous day, uses it as a background graph, and displays a graph for a current day written over the background graph using a color different from gray of the background graph.

With the activity amount-related information display apparatus according to the embodiment, on the display screen, the first display processing unit grays out the graph for the previous day, uses it as a background graph, and displays the graph for the current day written over the background graph using a color different from the gray of the background graph. As a result, when the exercise intensity, activity amount, or expended calories for a unit time of the current day is small with respect to the exercise intensity, activity amount, or expended calories for the unit time of the previous day of the measurement subject, the gray background graph is exposed outward in the radial direction of the graph of the current day. Accordingly, the user can intuitively know that the exercise intensity, activity amount, or expended calories for each unit time of the current day is small compared to the exercise intensity, activity amount, or expended calories for each unit time of the previous day of the measurement subject.

An activity amount-related information display apparatus according to an embodiment includes:

a target value setting unit configured to acquire an achieved value for exercise intensity, activity amount, or expended calories of the measurement subject for a past period prior to the one day that serves as a target period, and based on the achieved value, set a target value for exercise intensity, activity amount, or expended calories for the one day of the measurement subject;

an achievement degree acquisition unit configured to, based on the value information, calculate and acquire an achievement degree with respect to the target value for the exercise intensity, activity amount, or expended calories of the measurement subject for the one day; and a digital display processing unit configured to display the achievement degree as a numerical value on the display screen.

In the present specification, "based on the achieved value" of the past period includes the case where the target value is calculated by performing an arithmetic operation on the achieved value for the past period. For example, if the length of the past period and the length of the target period are different, the target value for the target period may be calculated according to the length of the target period by converting the achieved value for the past period using the number of days. If the length of the past period and the length of the target period are equal, the target value for the target period may be set to be equal to the achieved value for the past period.

With the activity amount-related information display apparatus according to the embodiment, the target value setting unit acquires the achieved value for the exercise intensity, activity amount, or expended calories of the measurement subject for a past period prior to the one day serving as the target period, and based on that achieved value, sets the target value for the exercise intensity, activity amount, or expended calories for the one day of the measurement subject. Based on the value information, the achievement degree acquisition unit calculates and acquires the achievement degree with respect to the target value for the exercise intensity, activity amount, or expended calories of the measurement subject for the one day. The digital display processing unit displays the achievement degree as a numerical value on the display screen. As a result, by looking at the numerical value, the user can know the exact achievement degree for the one day with respect to the target value based on the achieved value for the past period.

In another aspect, an activity amount-related information display apparatus of the present invention is an activity amount-related information display apparatus for displaying information relating to an activity amount of a measurement subject as a graph on a display screen, including:

an achievement degree acquisition unit configured to acquire an achievement degree with respect to a target value for exercise intensity, activity amount, or expended calories over a certain target period of the measurement subject; and a second display processing unit configured to, on the display screen, set a dark-colored circle, a white or daylight-colored ring-shaped region surrounding the circle in a ring shape, and a dark-colored background region surrounding the ring-shaped region, and display the ring-shaped region with a radial direction dimension varied according to the achievement degree, in which a brightness of the ring-shaped region gradually decreases moving outward in a radial direction so as to be continuous with the brightness of the background region.

In the present specification, the "dark color" of the circle and the background region means a color with a lower brightness than the "white or daylight color" of the ring-shaped region.

With the activity amount-related information display apparatus of the present invention, the achievement degree acquisition unit acquires the achievement degree with respect to the target value for the exercise intensity, activity amount, or expended calories (target value relating to activity amount) over a certain target period of the measurement subject. On the display screen, for the target period, the second display processing unit displays a dark-colored circle, a white or daylight-colored ring-shaped region surrounding the circle in the form of a ring, and a dark-colored background region around the ring-shaped region, and displays the achievement degree by varying the radial direction dimension of the ring-shaped region according to the achievement degree. For example, if the achievement degree is small for a certain target period, the radial direction dimension of the ring-shaped region will be small. If the achievement degree is large for another target period, the radial direction dimension of the ring-shaped region will be large. Moreover, the brightness of the ring-shaped region gradually decreases moving outward in the radial direction so as to be continuous with the brightness of the background region. Accordingly, the ring-shaped region displayed on the display screen looks like a solar corona. That is, if the achievement degree is small as a result of the measurement subject performing weak exercise for a certain target period, it will look like the sun is burning dimly. If the achievement degree is large as a result of the measurement subject performing vigorous exercise for another target period, it will look like the sun is burning brightly. The intensity with which the sun burns suggests to the user the exercise intensity and degree of energy expenditure due to exercise of the measurement subject. Accordingly, the user can intuitively know the achievement degree with respect to the target value relating to the activity amount of the measurement subject.

The "radial direction dimension" corresponding to the achievement degree need only correspond to the achievement degree over the entire circumference of the circle. In other words, the "radial direction dimension" of the ring-shaped region may have fluctuations around the circle. In the case of having such fluctuations, the ring-shaped region displayed on the display screen looks more like a solar corona.

Note that the achievement degree acquisition unit may input the exercise intensity, activity amount, or expended calories over the target period of the measurement subject, divide the input exercise intensity, activity amount, or expended calories by the target value, and thereby calculate and acquire the achievement degree.

An activity amount-related information display apparatus according to an embodiment includes an image storage unit configured to store a plurality of candidate images each having a different radial direction dimension, with which the ring-shaped region is to be displayed and; and an image selection unit configured to, among the plurality of candidate images, select a candidate image having a radial direction dimension corresponding to the achievement degree for the target period.

With the activity amount-related information display apparatus according to the embodiment, the image storage unit stores a plurality of candidate images each having a different radial direction dimension, with which the ring-shaped region is to be displayed. From among the plurality of candidate images, the image selection unit selects a candidate image having a radial direction dimension corresponding to the achievement degree for the target period. Accordingly, an image including the ring-shaped region can be easily displayed on the display screen.

An activity amount-related information display apparatus according to an embodiment includes a target value setting unit configured to acquire an achieved value for exercise intensity, activity amount, or expended calories of the measurement subject for a past period prior to the target period, and based on the achieved value, set the target value for the target period of the measurement subject.

With the activity amount-related information display apparatus according to the embodiment, the target value setting unit acquires the achieved value for the exercise intensity, activity amount, or expended calories of the measurement subject for the past period prior to the target period, and based on the achieved value, sets the target value for the exercise intensity, activity amount, or expended calories for the target period of the measurement subject. As a result, by looking at the ring-shaped region displayed on the display screen, the user can intuitively know the achievement degree for the target period with respect to the target value based on the achieved value for the past period.

As is clear from the description above, with the activity amount-related information display apparatus according to the present invention, information relating to an activity amount for each unit time of a measurement subject in one day can be displayed on a display screen such that it is easy to understand intuitively. Also, with the activity amount-related information display apparatus according to the present invention, an achievement degree with respect to a target value relating to an activity amount of a measurement subject can be displayed on a display screen such that it is easy to understand intuitively.

DETAILED DESCRIPTION OF THE PREFERRED EMBODIMENTS

Hereinafter, an embodiment of the present invention will be described in detail with reference to the drawings.

Figure 1:
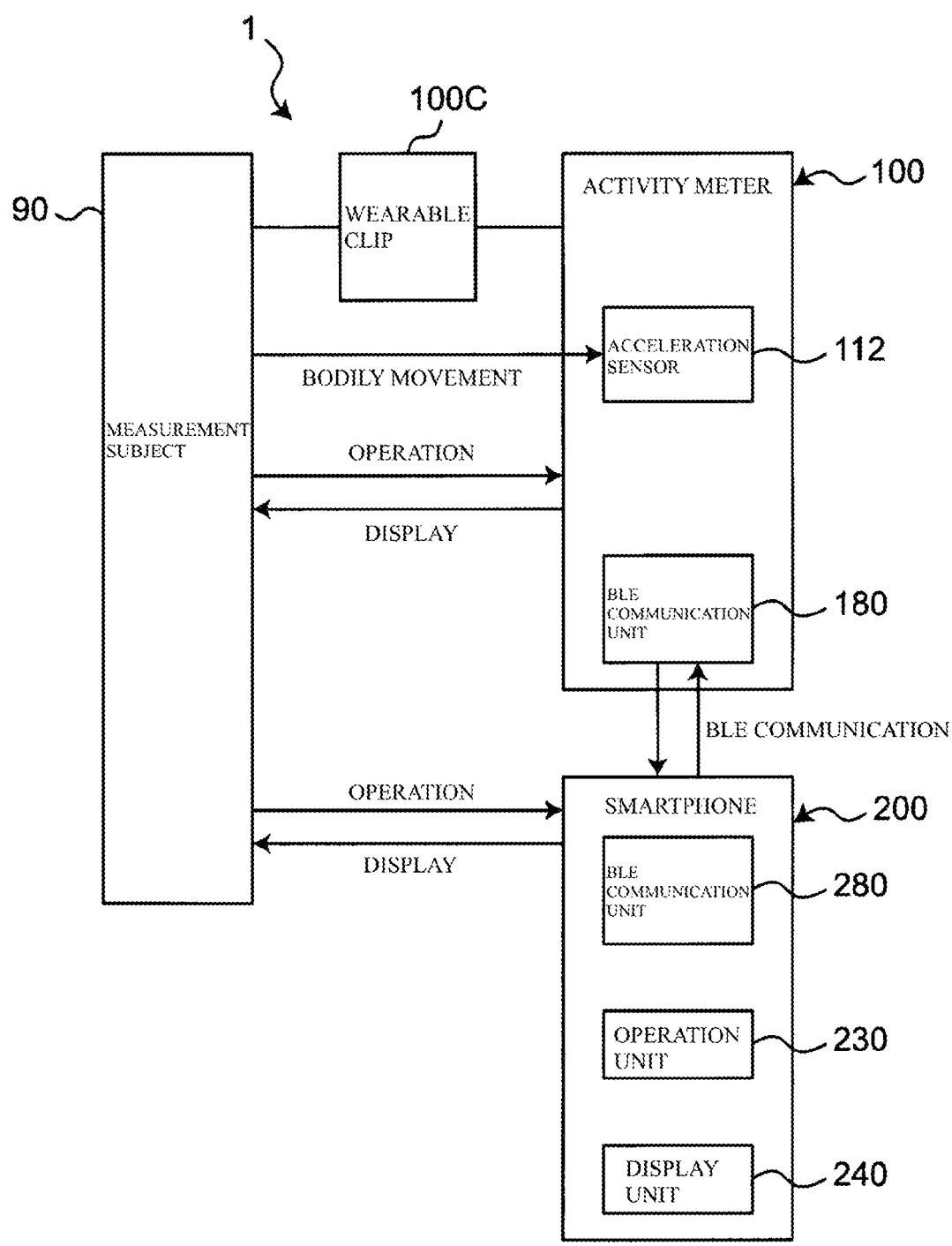
FIG. 1 is a diagram showing a system configuration of an activity amount-related information display apparatus according to an embodiment of the present invention.

FIG. 1 shows a system configuration of an activity amount-related information display apparatus (indicated overall by reference numeral 1) according to an embodiment of the present invention. The activity amount-related information display apparatus 1 includes an activity meter 100 and a smartphone 200. In the current example, the activity meter 100 and the smartphone 200 can communicate with each other using BLE (Bluetooth low energy) communication.

Figure 2:
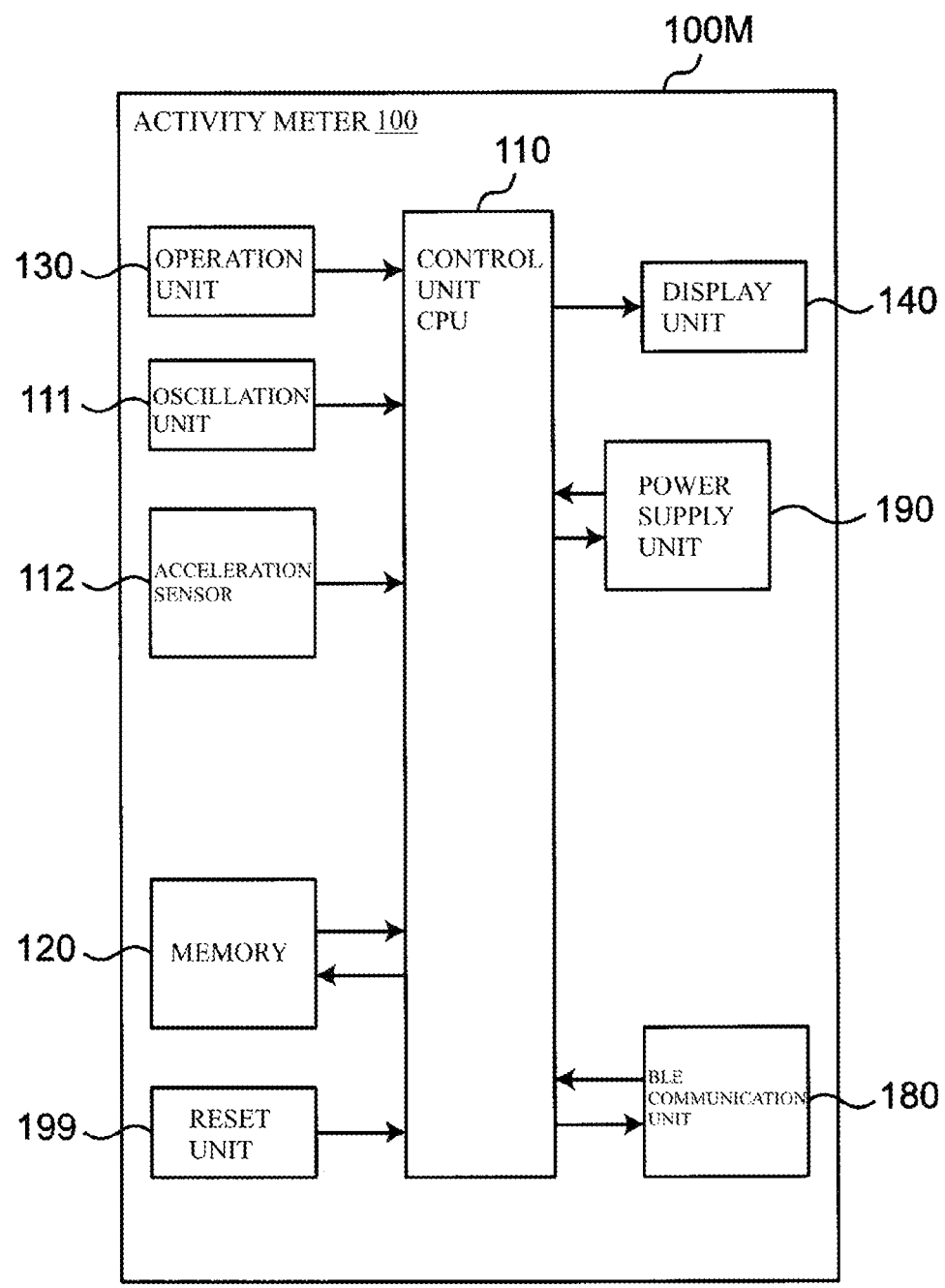
FIG. 2 is a diagram showing a block configuration of an activity meter included in the system.

As shown in FIG. 2, the activity meter 100 includes a casing 100M, and a control unit 110, an oscillation unit 111, an acceleration sensor 112, a memory 120, an operation unit 130, a display unit 140, a BLE communication unit 180, a power supply unit 190, and a reset unit 199, which are mounted in the casing 100M.

The casing 100M is formed so as to be of a size that fits in the palm of a person's hand, so that the activity meter 100 is easy to carry.

The oscillation unit 111 includes a crystal resonator and generates a clock signal that serves as a reference for the timing of operations of the activity meter 100.

The acceleration sensor 112 detects acceleration in three axes (three directions) received by the casing 100M and outputs the acceleration to the control unit 110.

The memory 120 includes a ROM (Read Only Memory) and a RAM (Random Access Memory). The ROM stores data of programs for controlling the activity meter 100. Also, the RAM stores setting data for setting various functions of the activity meter 100, data of acceleration measurement results and calculation results, and the like.

The control unit 110 includes a CPU (Central Processing Unit) that operates based on the above-described clock signal, and controls the units (including the memory 120, display unit 140, and BLE communication unit 180) of the activity meter 100 based on the detection signal from the acceleration sensor 112, in accordance with the programs for controlling the activity meter 100 stored in the memory 120.

In this example, the operation unit 130 is composed of button switches and receives appropriate input of operations, such as an operation for switching the power supply on/off, an operation for switching the display content, input of the sex and body weight of the measurement subject, and the like.

In this example, the display unit 140 includes a display screen composed of an LCD (liquid crystal display) or an organic EL (electroluminescence) display, and displays predetermined information in accordance with a signal received from the control unit 110 on the display screen.

In this example, the power supply unit 190 is composed of a rechargeable battery and supplies power to the units of the activity meter 100.

The BLE communication unit 180 communicates with the smartphone 200. For example, the BLE communication unit 180 transmits information indicating a measurement result or the like to the smartphone 200. Also, the BLE communication unit 180 receives operation instructions from the smartphone 200.

In this example, the reset unit 199 resets and initializes the operation of the control unit 110 and the content stored in the memory 120 in accordance with input received through the operation unit 130.

Figure 3:
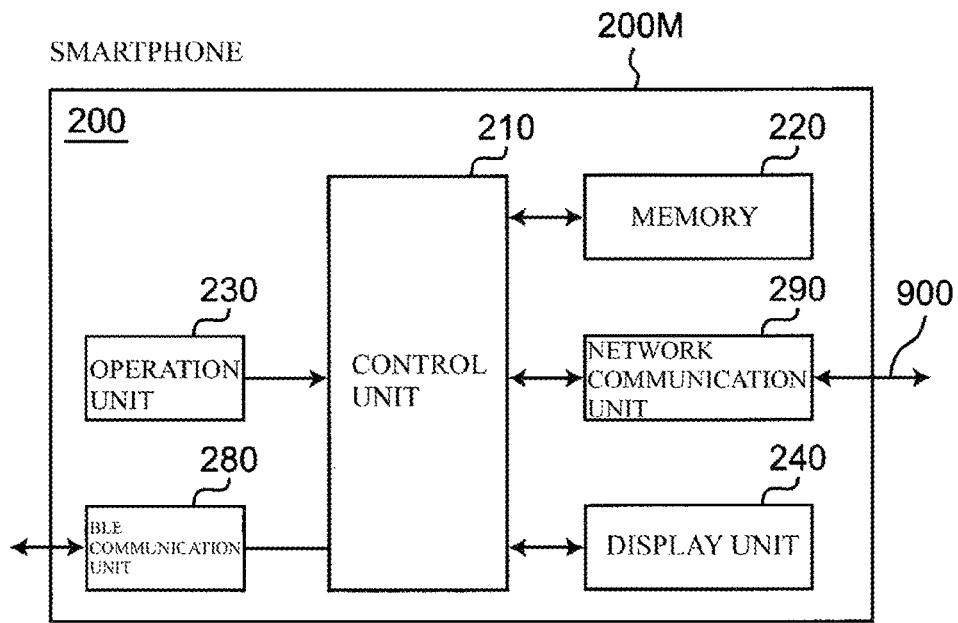
FIG. 3 is a diagram showing a block configuration of a smartphone included in the system.

As shown in FIG. 3, the smartphone 200 includes a main body 200M, and a control unit 210, a memory 220, an operation unit 230, a display unit 240, a BLE communication unit 280, and a network communication unit 290, which are mounted in the main body 200M. The smartphone 200 is a commercially-available smartphone in which application software (hereinafter referred to as an "activity amount-related information display program") is installed so as to cause display of information relating to the activity amount.

The control unit 210 includes a CPU and auxiliary circuits thereof, controls the units of the smartphone 200, and executes processing in accordance with programs and data stored in the memory 220. That is, the control unit 210 processes data input from the operation unit 230 and the communication units 280 and 290, stores the processed data in the memory 220, displays the processed data with the display unit 240, and causes it to be output from the communication units 280 and 290.

The memory 220 includes a RAM used as a work region needed for executing programs with the control unit 210, and a ROM for storing basic programs to be executed by the control unit 210. Also, a semiconductor memory (memory card, SSD (Solid State Drive)) or the like may be used as a storage medium of an auxiliary storage apparatus for assisting the storage region of the memory 220. In this example, as an image storage unit, the memory 220 stores multiple later-described candidate images to be displayed on the display unit 240 in a later-described second display example in advance.

In this example, the operation unit 230 is composed of a touch panel provided on the display unit 240. Note that the operation unit 230 may include other hardware operation devices such as a keyboard.

The display unit 240 includes a display screen (e.g., composed of an LCD or organic EL display). The display unit 240 is controlled by the control unit 210 and displays predetermined images on a display screen.

The BLE communication unit 280 communicates with the activity meter 100. For example, the BLE communication unit 280 transmits operation instructions to the activity meter 100. Also, the BLE communication unit 280 receives information indicating a measurement result or the like from the activity meter 100.

The network communication unit 290 can transmit information from the control unit 210 to another apparatus via the network 900, as well as receive information transmitted via the network 900 from another apparatus and transfer the received information to the control unit 210.

Figure 4:
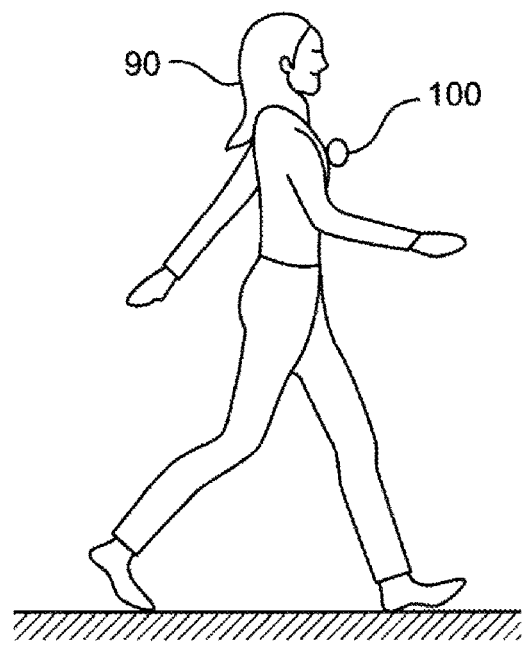
FIG. 4 is a diagram showing a state in which a measurement subject is walking while wearing an activity meter.

For example, as shown in FIG. 4, if the activity amount-related information display apparatus 1 is used by a measurement subject 90 serving as a user, for example, the activity meter 100 is worn on the chest, for example, of the measurement subject 90 using a wearable clip 100C (shown in FIG. 1). As a result, the exercise of the measurement subject 90 is the output of the acceleration sensor 112.

In the case of performing measurement, the measurement subject 90 turns on the power supply of the activity meter 100 and instructs the activity meter 100 to start measurement. Then, the measurement subject 90 performs one or multiple days of activity.

Thereafter, the control unit 110 of the activity meter 100 receives the output from the acceleration sensor 112 and calculates the exercise intensity (unit: [METs]), activity amount (unit: [Ex]), and the expended calories (unit: [kcal]) for each unit time $\Delta t$ (in this example, $\Delta t=10$ minutes) according to the activity of the measurement subject (if the exercise intensity or the like changes in the unit time $\Delta t$, the average value in that unit time $\Delta t$ is calculated). Herein, i) the exercise intensity (unit: [METs]) is an amount indicating the ratio of the exercise intensity with respect to the exercise intensity during the resting time.

ii) The activity amount (unit: [Ex]) is an amount obtained by multiplying the exercise intensity [METs] by the amount of time (unit: [h]; hours) for which the exercise was performed. That is, [Ex]=[METs·h].

iii) Expended calories (unit: [kcal]) are obtained by multiplying the activity amount [Ex] by the body weight [kg] of the body. That is, they are calculated as expended calories [kcal]=activity amount [Ex]×body weight [kg]. Note that the body weight of the measurement subject 90 is input in advance through the operation unit 130 and stored in the memory 120.

Data (value information) indicating the calculated exercise intensity (unit: [METs]), activity amount (unit: [Ex]), and expended calories (unit: [kcal]) for each unit time $\Delta t$ is sequentially stored and accumulated in the memory 120.

If the measurement subject 90 starts up the activity amount-related information display program of the smartphone 200 while the activity meter 100 is on, the control unit 210 of the smartphone 200 functions as a value information acquisition unit and, via the BLE communication unit 280, receives the data indicating the exercise intensity (unit: [METs]), the activity amount (unit: [Ex]), and the expended calories (unit: [kcal]) for each unit time Δt from the activity meter 100 (via the BLE communication unit 180). The received data is stored in the memory 220.

Note that the measurement subject 90 may input his/her body weight via the operation unit 230 of the smartphone 200 in a state in which an activity amount-related information display program of the smartphone 200 has been started up. Alternatively, if the other apparatus has information indicating the body weight of the measurement subject 90, the control unit 210 of the smartphone 200 may receive information indicating the body weight via the network 900 and the network communication unit 290. Then, the control unit 210 of the smartphone 200 may calculate the expended calories [kcal].

First Display Example

Figure 5:
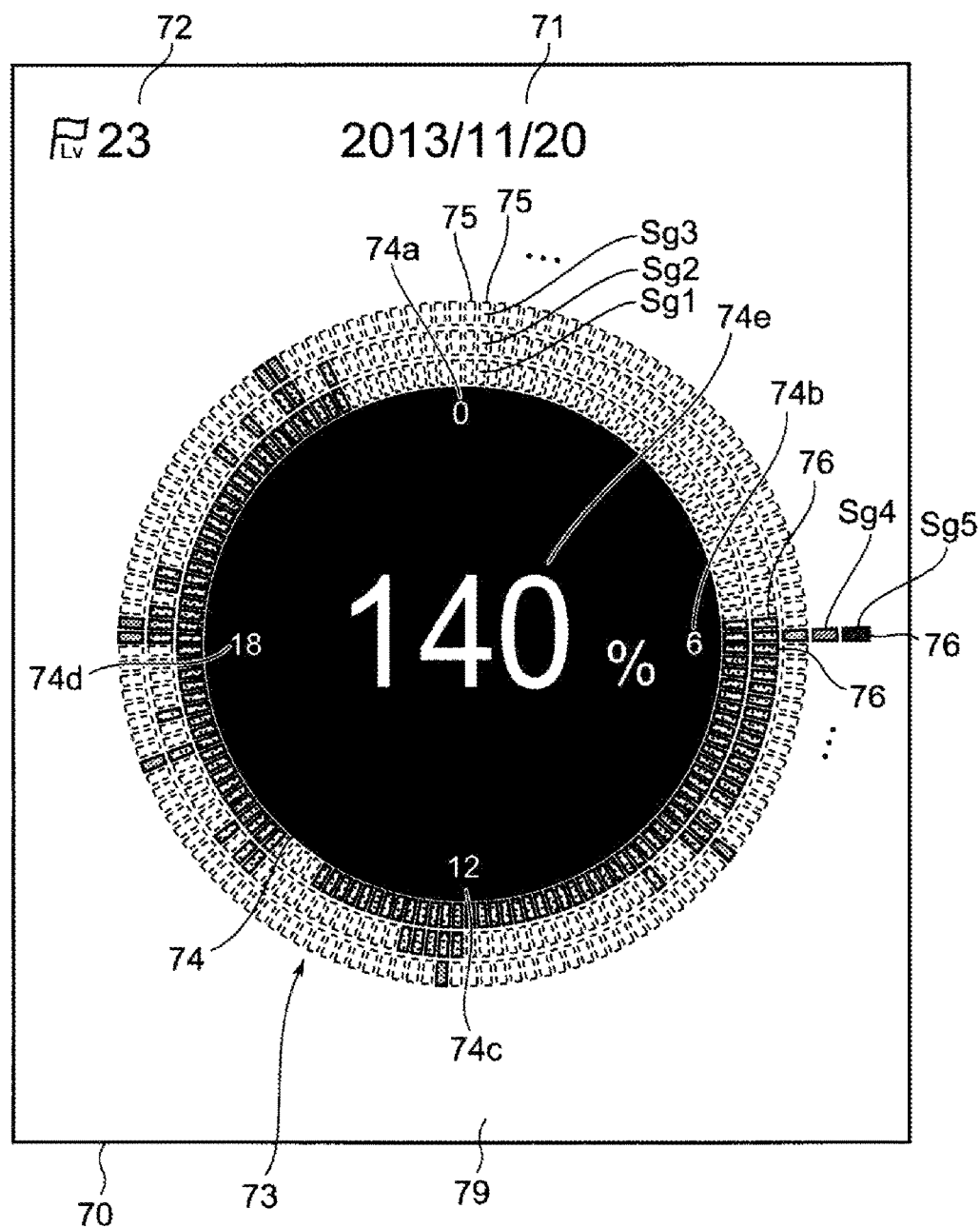
FIG. 5 is a diagram illustrating an image displayed on a display screen of the smartphone in an "exercise intensity for each unit time in one day" mode.
Figure 6:
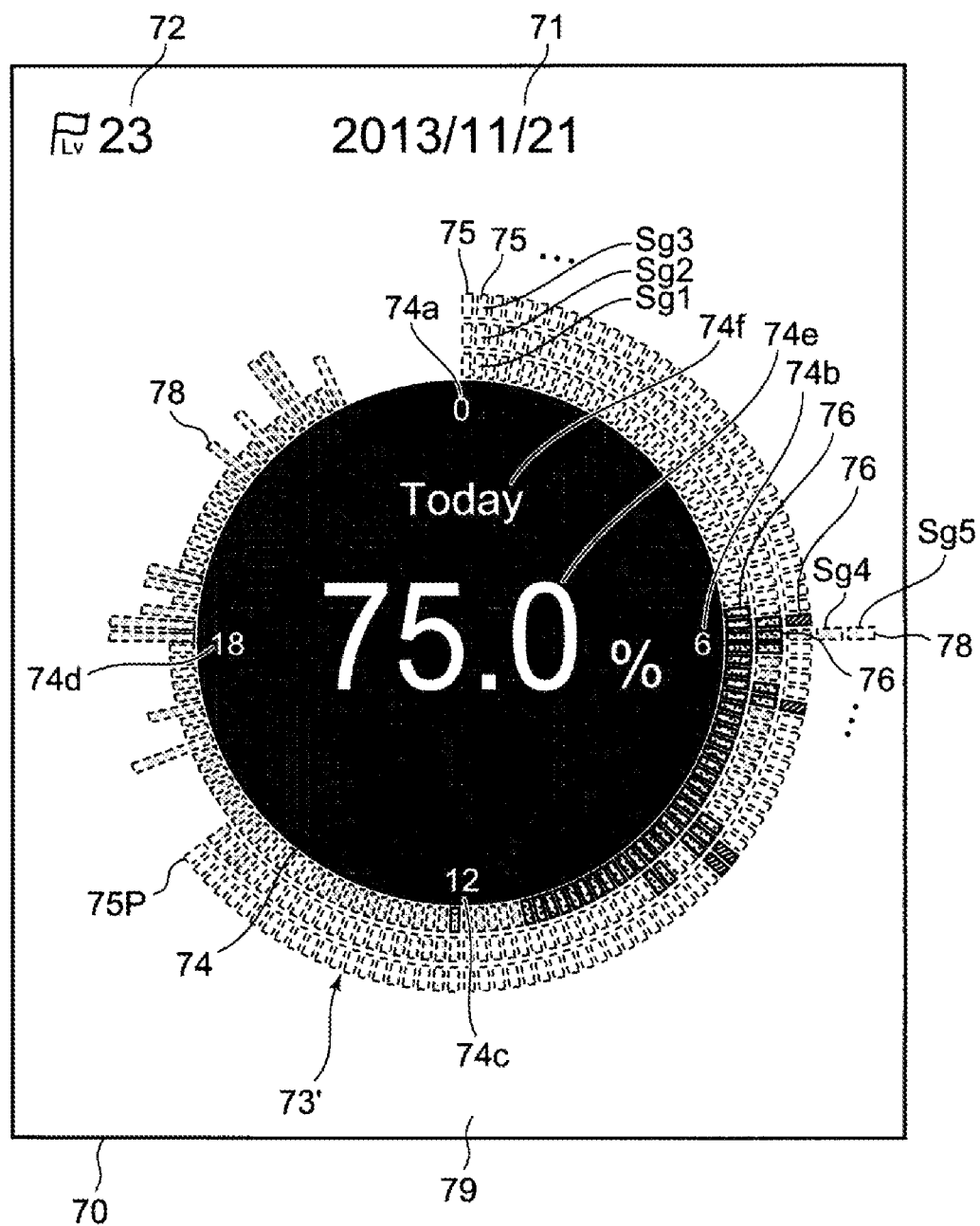
FIG. 6 is a diagram illustrating another image displayed on the display screen of the smartphone in an "exercise intensity for each unit time in one day" mode.

If the measurement subject 90 selects a mode of "exercise intensity for each unit time in one day", for example, in the activity amount-related information display program via the operation unit 230 of the smartphone 200, the control unit 210 functions as a first display processing unit, uses the above-described data to create an image such as those shown in FIGS. 5 and 6, and displays the image on the display screen 70 of the display unit 240.

FIG. 5 shows an example of an image including a graph created using data of a day (a day's worth of data) prior to the operation day (the current day). In the center of the upper portion of the display screen 70, a date field 71 indicating the date of that day (in this example, 2013/11/20 (Nov. 20, 2013)) is provided. On the left side of the upper portion of the display screen 70, an active level field 72 indicating the target value for the activity amount for one week (in this example, seven days starting from Sunday and including Nov. 20, 2013), which was set in advance by the measurement subject, is provided. The activity amount target value (in this example, 23 [Ex]) in the active level field 72 is set by a user performing input thereof to the memory 220 of the smartphone 200 in advance via the operation unit 230.

Also, a graph 73 indicating the exercise intensity for each unit time in one day is displayed in the center of the display screen 70. In this example, on the display screen 70, a circle 74 corresponding to one day is set, and time divisions 75, 75, . . . each indicating the elapse of the unit time Δt in one day are set clockwise around the circle 74. The time divisions 75 are bars that extend outward in the radial direction about the circle 74 and are each divided into three segments Sg1, Sg2, and Sg3 in the radial direction. The segments Sg1, Sg2, and Sg3 are shown as broken-line frames that are approximately rectangular in the present example. "0" o'clock, "6" o'clock, "12" o'clock, and "18" o'clock are displayed as numerals respectively in an upper edge portion 74a, a right edge portion 74b, a lower edge portion 74c, and a left edge portion 74d of the circle 74.

The achievement degree (140% in this example) with respect to the activity amount target value for one day, which serves as the target period, is displayed as a numeral in a central portion 74e of the circle 74. The activity amount target value for one day is set as 3.3 [Ex] by the control unit 210 functioning as a target value setting unit and dividing the activity amount target value 23 [Ex] in the active level field 72 by the number of days 7 in the week (conversion using the number of days) (note that the activity amount has two significant figures; the same follows below). Also, based on the above-described received data, the control unit 210 functions as an achievement degree acquisition unit to calculate the achievement degree with respect to the activity amount target value for one day, and the control unit 210 functions as a digital display processing unit to display the calculated achievement degree.

In this example, the graph 73 displays exercise intensities (unit: [METs]) serving as value information as groups of bars 76, 76, . . . that extend outward in the radial direction around a circle and have lengths of multiple levels (5 levels in this example), each length corresponding to a value indicated by the exercise intensity for a unit time (10 minutes in this example).

Figure 7:
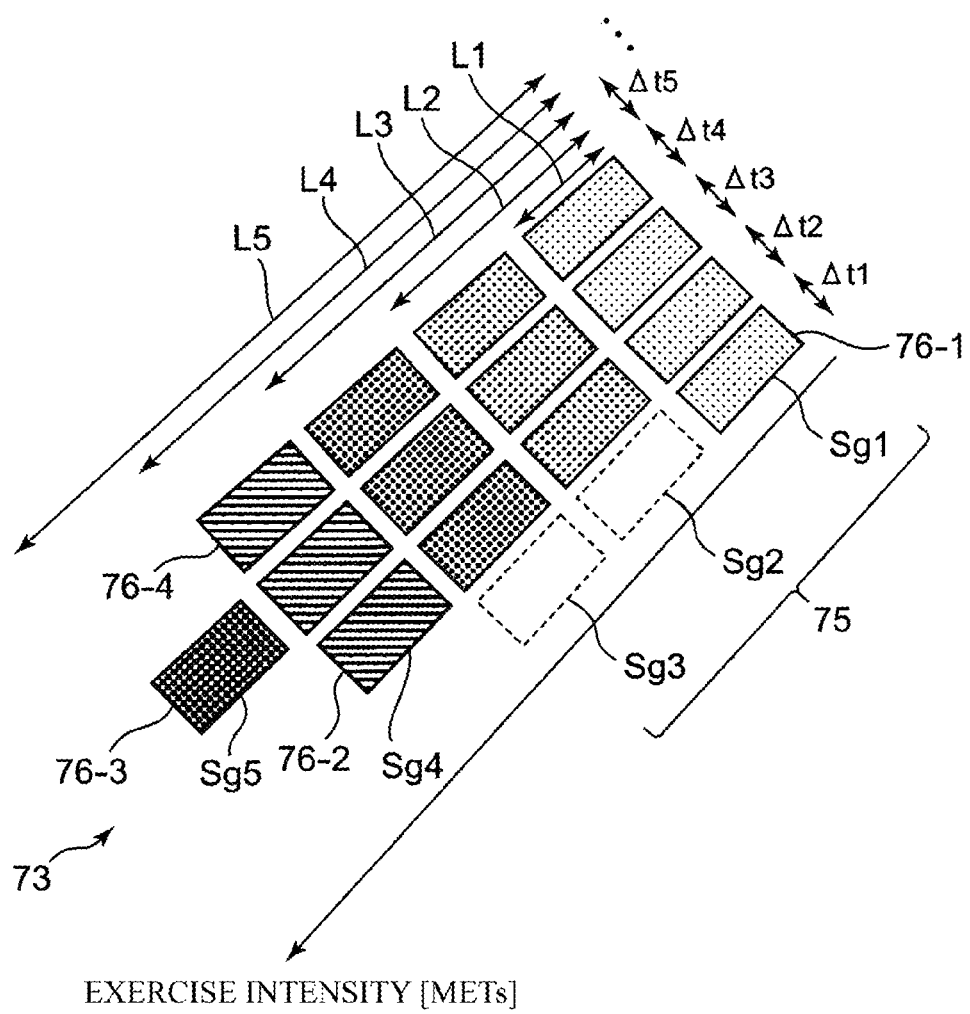
FIG. 7 is a diagram for describing the meaning of the display of the graphs shown in FIGS. 5 and 6.
Figure 8B:
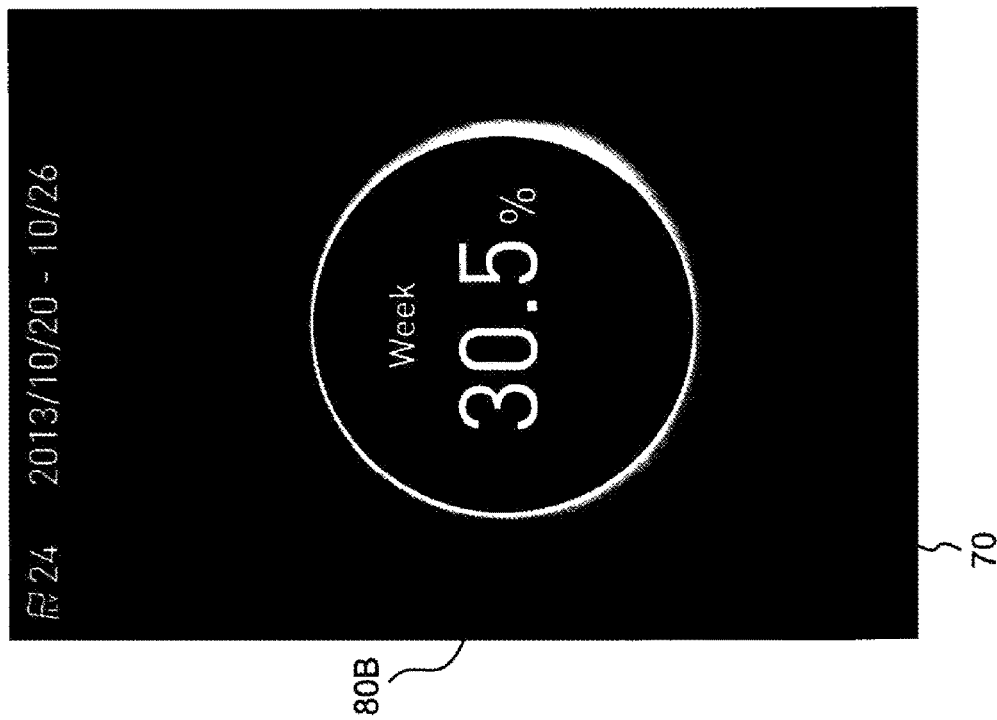
FIGS. 8A and 8B are diagrams each showing an image displayed on the display screen of the smartphone in an "activity amount achievement degree for one week" mode.
Figure 8A:
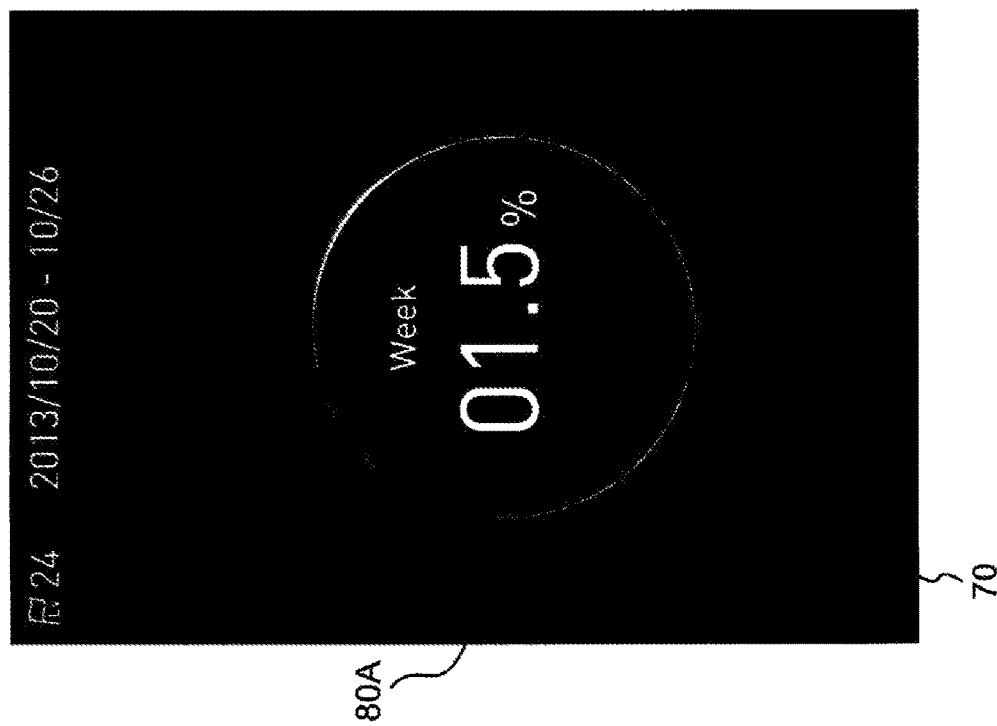
Figure 9B:
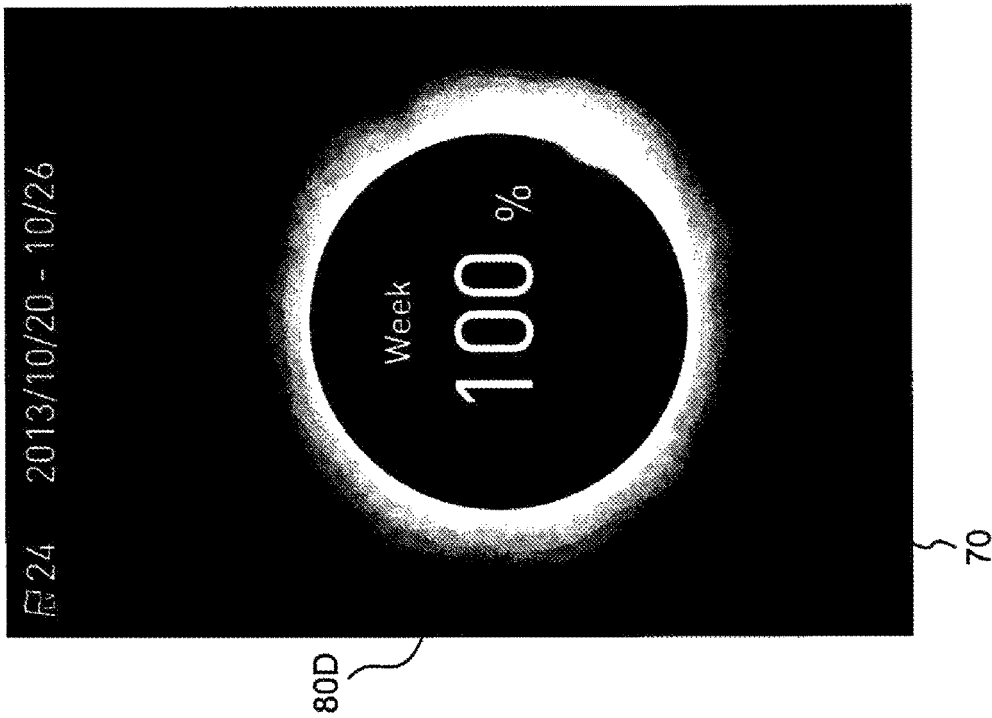
FIGS. 9A and 9B are diagrams each illustrating another image displayed on the display screen of the smartphone in an "activity amount achievement degree for one week" mode.
Figure 9A:
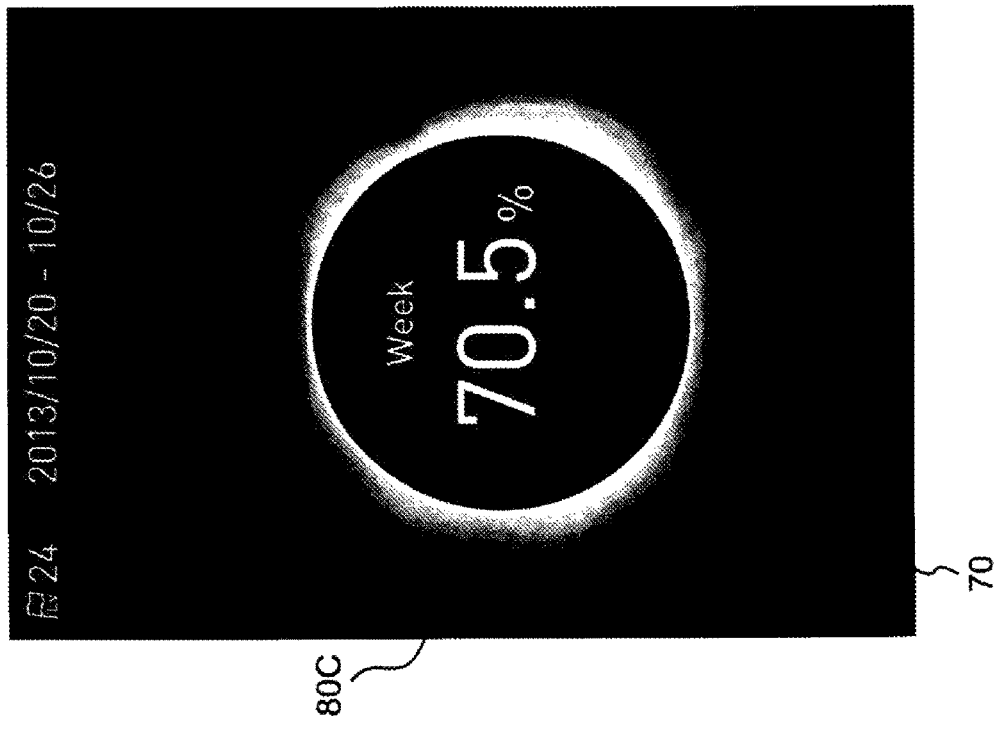

FIG. 7 shows an enlarged view of a portion of the graph 73 (a portion corresponding to around 15 o'clock in the lower left portion of the circle 74) in order to describe a method of rendering the graph 73. In FIG. 7, numerals are added to Δt so that the elapse of the unit time Δt is indicated as Δt1, Δt2, Δt3, Δt4, . . . . The time divisions 75, or in other words, the three segments Sg1, Sg2, and Sg3, are displayed in a mode of solid-line or broken-line frames that are approximately rectangular (as will be described later, a broken-line frame indicates that the length of a bar 76 has not reached that frame) for the unit times Δt1, Δt2, Δt3, and Δt4 that have already elapsed. The time division 75 (approximately rectangular frames indicating three segments) is not displayed for the unit time Δt5 that has not elapsed.

Also, in FIG. 7, the bars 76 that indicate the exercise intensities are individually specified as 76-1, 76-2, 76-3, and 76-4 by adding branch numbers to each of the unit times Δt1, Δt2, Δt3, and Δt4. As described above, a bar 76 (indicating any of 76-1 to 76-4) can have the length L1, L2, L3, L4, or L5, which are multiple levels (5 levels in this example) corresponding to the value indicated by the exercise intensity, in the radial direction. In this example, the bars 76 are divided into segments Sg1, Sg2, Sg3, Sg4, and Sg5 for each level in the radial direction (exercise intensity). The shapes of the segments Sg1, Sg2, and Sg3, which are the bottom three levels (first level to third level) of the bars 76 respectively match the shapes of the three segments Sg1, Sg2, and Sg3 of the time divisions 75 (for the sake of simplicity, the same reference numerals are used for the segments of the bars 76 and the segments of the time divisions 75). The shapes of the segments Sg4 and Sg5 of the top two levels (fourth level and fifth level) of the bars 76 correspond to shapes obtained by adding approximately rectangular solid-line frames that are substantially the same as the segments Sg1, Sg2, and Sg3 outward in the radial direction.

In this example, the five levels of the exercise intensity are divided according to the rules indicated in Table 1 below. That is, the first level of the exercise intensity indicates being within a range of 0 METs to 2.9 METs, and a resting or approximately resting state is assumed as the mode of exercise. The second level indicates being within a range of 3.0 METs to 4.2 METs, and walking is assumed as the mode of exercise. The third level indicates being within a range of 4.3 METs to 6.9 METs, and fast walking is assumed as the mode of exercise. The fourth level indicates being within a range of 7.0 METs to 7.9 METs, and jogging is assumed as the mode of exercise. The fifth level indicates 8.0 METs or more, and going upstairs (stair-climbing exercise) is assumed as the method of exercise.

TABLE 1

| Exercise intensity level | Range of exercise intensity (unit: [METs]) | Mode of exercise | Color added to segment |
| --- | --- | --- | --- |
| First level | 0 to 2.9 | Resting or approximately resting | Green |
| Second level | 3.0 to 4.2 | Walking | Green |
| Third level | 4.3 to 6.9 | Fast walking | Blue |
| Fourth level | 7.0 to 7.9 | Jogging | Purple |
| Fifth level | 8.0 or more | Stair-climbing | Pink |

(METs in Table 1 have two significant figures.)

In this example, the segments Sg1, Sg2, Sg3, Sg4, and Sg5 of the bars 76 are colored in accordance with the rules indicated in the right column of Table 1. That is, the segments Sg1 and Sg2 of the first level and the second level are colored green. This is because green is associated with a calm state in which the exercise intensity is relatively low. The segment Sg3 of the third level is colored blue. The segment Sg4 of the fourth level is colored purple. The segment Sg4 of the fifth level is colored pink. Thus, in this example, the segments Sg3, Sg4, and Sg5 of the third level to the fifth level are colored with colors having progressively higher color temperatures as the level increases. Hereinafter, for the sake of understandability, a bar that is colored will be referred to as a "colored bar".

Note that all of the segments Sg1, Sg2, Sg3, Sg4, and Sg5 of the five levels may be colored with colors having progressively higher color temperatures as the level increases.

In the example shown in FIG. 7, a colored bar 76-1 of the unit time Δt1 has a length L1, and indicates that the exercise intensity was the first level. The segment Sg1 of the colored bar 76-1 is colored green. On the other hand, in accordance with the fact that the length of the colored bar 76-1 did not reach the segments Sg2 and Sg3 of the location of the unit time Δt1, only the approximately rectangular broken-line frames thereof are displayed in this example, and the insides of the frames are white (same as the color of a background 79 of the display screen 70 in FIG. 5). A colored bar 76-2 of the unit time Δt2 has a length L4 and indicates that the exercise intensity was the fourth level. The segments Sg1, Sg2, Sg3, and Sg4 of the bar 76-2 are colored green, green, blue, and purple respectively. The colored bar 76-3 of the unit time Δt3 has a length L5 and indicates that the exercise intensity was the fifth level. The segments Sg1, Sg2, Sg3, Sg4, and Sg5 of the bar 76-3 are colored green, green, blue, purple, and pink respectively. Also, the colored bar 76-4 of the unit time Δt4 is displayed similarly to the colored bar 76-2 of the unit time Δt2.

Thus, in this example, if the value indicated by the exercise intensity is small as a result of the measurement subject 90 performing weak exercise for a unit time Δt, a short colored bar 76 will be displayed. On the other hand, if the value indicated by the exercise intensity is large as a result of the measurement subject 90 performing vigorous exercise for another unit time Δt, a long colored bar 76 will be displayed. Accordingly, the user can intuitively know the exercise intensity for each unit time as information relating to the activity amount for each unit time of the measurement subject in one day.

In particular, in this example, if the value indicated by the exercise intensity is small as a result of the measurement subject 90 performing weak exercise for a unit time Δt, the length of the bar 76 will be short, there will be a small number of segments, and all of the segments will be colored with colors having low color temperatures. On the other hand, if the value expressed by the value information is large as a result of the measurement subject 90 performing vigorous exercise for another unit time, the length of the bar 76 will be long, there will be a higher number of segments, and high-level segments will be colored with colors having high color temperatures. The "color temperature" in this context suggests to the user the exercise intensity and the degree of energy expenditure due to exercise of the measurement subject 90. Accordingly, the user can more intuitively know the exercise intensity of the measurement subject 90 for each unit time.

Also, in this example, the circle 74 (not a circular arc) corresponding to one day is set on the display screen 70. "0" o'clock, "6" o'clock, "12" o'clock, and "18" o'clock are respectively displayed as numerals in the upper end portion 74a, the right end portion 74b, the lower end portion 74c, and the left end portion 74d of the circle 74. Accordingly, the time divisions 75 look like divisions of an analog 24-hour clock. Accordingly, the user can intuitively know that the exercise intensities displayed on the display screen 70 are pieces of information for one day.

Note that instead of the circle 74, it is possible to set a circular arc corresponding to one day on the display screen 70 and to display, around the circular arc, time divisions 75 and bars 76, 76, . . . , which extend outward in the radial direction and have lengths of multiple levels, the lengths each corresponding to a value indicated by the exercise intensity for a unit time.

FIG. 6 illustrates, as an example, an image including a graph of the "exercise intensity for each unit time in one day", which is created using the data of the operation day (the current day; in this example, Nov. 21, 2013) and the day before that (in this example, Nov. 20, 2013). In FIG. 6, elements that are the same as the elements shown in FIG. 5 are denoted by the same reference numerals. Thus, redundant description is not included. In FIG. 6, "Today" (current day) is displayed in the portion 74f between the upper portion 74a and the central portion 74e of the circle 74 due to the fact that data of the operation day (current day) is being used. Moreover, in this example, the time divisions 75 (approximately rectangular frames showing three segments) are displayed from 0 o'clock to the current time 15:30 (time division 75P).

In this example, the graph 73 of the previous day (portion to which solid-line frames have been added in FIG. 5) is grayed out and used as a background graph 78 on the display screen 70. A graph 73' for the current day is displayed written over the background graph 78 in accordance with the rules described using Table 1 (regarding the length and color of the bars 76). That is, the graph 73' of the current day is displayed with colors that are different from the color (gray) of the background graph 78.

As a result, when the exercise intensity for a unit time of the current day is smaller than the exercise intensity for the unit time of the previous day of the measurement subject 90, the gray background graph 78 is exposed outward in the radial direction from the graph 73' of the current day. Accordingly, the user can intuitively know when the exercise intensity for a unit time of the current day is smaller than the exercise intensity for the unit time of the previous day of the measurement subject 90. As a result, for example, it is easier for the user to prompt the measurement subject 90 to perform more vigorous exercise.

Moreover, the achievement degree (in this example, 75.0%) up to the current time 15:30 with respect to the activity amount target value for one day for the current day is displayed as a numerical value in the central portion 74e of the circle 74 using the same method as in the case of FIG. 5. Accordingly, the user can know the exact achievement degree for the current day with respect to the activity amount target value for one day by looking at this numerical value (display in units of %). As a result, for example, it is easy for the user to prompt the measurement subject 90 to perform more vigorous exercise.

In the above-described example, the activity amount target value for the above-described active level field 72 is set by the user performing input thereof via the operation unit 230 to the memory 220 of the smartphone 200 in advance. However, there is no limitation to this, and for example, the control unit 210 may function as a target value setting unit to acquire the achieved value for the activity amount of the measurement subject 90 for a past week prior to the current day (e.g., the previous week) and set the activity amount target value based on this achieved value. For example, if the achieved value for the activity amount of the measurement subject 90 is 28 Ex for the previous week, the activity amount target value of the above-described active level field 72 for the current week may be set to be equal to the achieved value 28 Ex of the previous week. In this case, the activity amount target value for one day is set as 4.0 [Ex] by dividing the activity amount target value 28 [Ex] of the active level field 72 by the number of days 7 in one week (conversion using the number of days). As a result, by looking at the numerical value (displayed in units of %) in the central portion 74e of the circle 74, the user can know the exact achievement degree for the current day with respect to the activity amount target value for one day based on the achieved value for the previous week.

Note that, as understood by a person skilled in the art, there is no limitation to the "exercise intensity for each unit time in one day", and the "activity amount for each unit time in one day", or "expended calories for each unit time in one day" can also be displayed in modes similar to those of FIGS. 5 and 6 as the information relating to the activity amount for each unit time in one day of the measurement subject 90.

Second Display Example

For example, when the measurement subject 90 selects an "activity amount achievement degree for one week" mode for the activity amount-related information display program via the operation unit 230 of the smartphone 200, first, the control unit 210 functions as the achievement degree acquisition unit to acquire the achievement degree (in units of %; referred to as "activity amount achievement degree" as necessary) with respect to the predetermined target value for the activity amount over one week of the measurement subject 90. In this example, the target value is set by the user performing input thereof via the operation unit 230 to the memory 220 of the smartphone 200 in advance.

Figure 11:
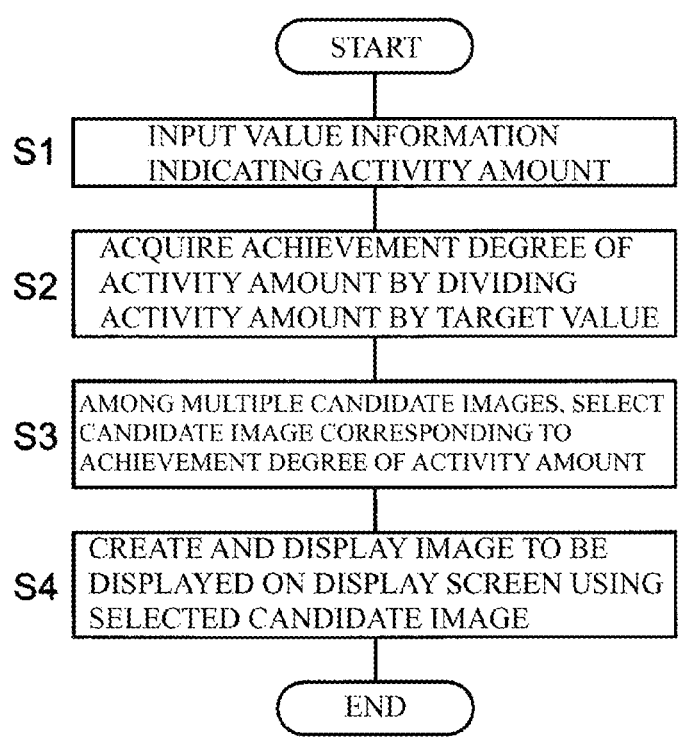
FIG. 11 is a diagram showing a flow of processing performed by a control unit of the smartphone in order to display the images shown in FIGS. 8A, 8B, 9A, and 9B.

Specifically, as shown in step S1 of FIG. 11, the control unit 210 of the smartphone 200 receives input of value information indicating the activity amount (accumulated value) over one week of the measurement subject 90 from the activity meter 100. Next, as shown in step S2, the activity amount indicated by the input value information is divided by the above-described target value (one-week activity amount target value). Accordingly, the activity amount achievement degree is calculated and acquired.

In this example, multiple candidate images 80A, 80B, 80C, 80D, . . . such as those shown in FIGS. 8A and 8B and FIGS. 9A and 9B are stored in the memory 220 of the smartphone 200. As shown schematically in FIG. 10 (corresponds to FIG. 9A), the candidate images each include a dark-colored (in this example, black) circle 84, a white (or daylight-colored) ring-shaped region 85 that surrounds the circle 84 in the form of a ring, and a dark-colored (in this example, black) background region 89 around the ring-shaped region 85. As shown in FIGS. 8A and 8B and FIGS. 9A and 9B, radial direction dimensions (height in the R direction) H of the ring-shaped regions 85 of the candidate images vary according to the activity amount achievement degrees (in this example, 1.5%, 30.5%, 70.5%, 100%) that are to be indicated by the respective candidate images 80A, 80B, 80C, and 80D, and sequentially increase in size. Like a solar corona, the brightness of the ring-shaped region 85 gradually decreases moving outward in the radial direction so as to be continuous with the brightness of the background region 89. Moreover, as shown schematically in FIG. 10, the radial direction dimension H of the ring-shaped region 85 has fluctuations 85a around the circle 84, like a solar corona.

In FIGS. 8A, 8B, 9A, and 9B, only four candidate images 80A, 80B, 80C, and 80D are shown for the sake of simplicity, but in this example, 11 candidate images with ring-shaped regions 85 having radial direction dimensions H that sequentially increase in size are prepared and stored in the memory 220. As will be described hereinafter, the 11 candidate images are selected when the acquired activity amount achievement degree (step S2 in FIG. 11) is 0% to 10%, 10% to 20%, 20% to 30%, 30% to 40%, 40% to 50%, 50% to 60%, 60% to 70%, 70% to 80%, 80% to 90%, 90% to 100%, and greater than 100%.

In step S3 of FIG. 11, the control unit 210 of the smartphone 200 functions as an image selection unit to select, among the multiple (in this example, 11) candidate images 80A, 80B, 80C, 80D, . . . , the candidate image corresponding to the activity amount achievement degree acquired in step S2.

Next, in step S4 of FIG. 11, the control unit 210 functions as a second display processing unit to create and display the image to be displayed on the display screen 70 as shown in FIGS. 8A and 8B and FIGS. 9A and 9B using the candidate image selected in step S3.

Figure 10:
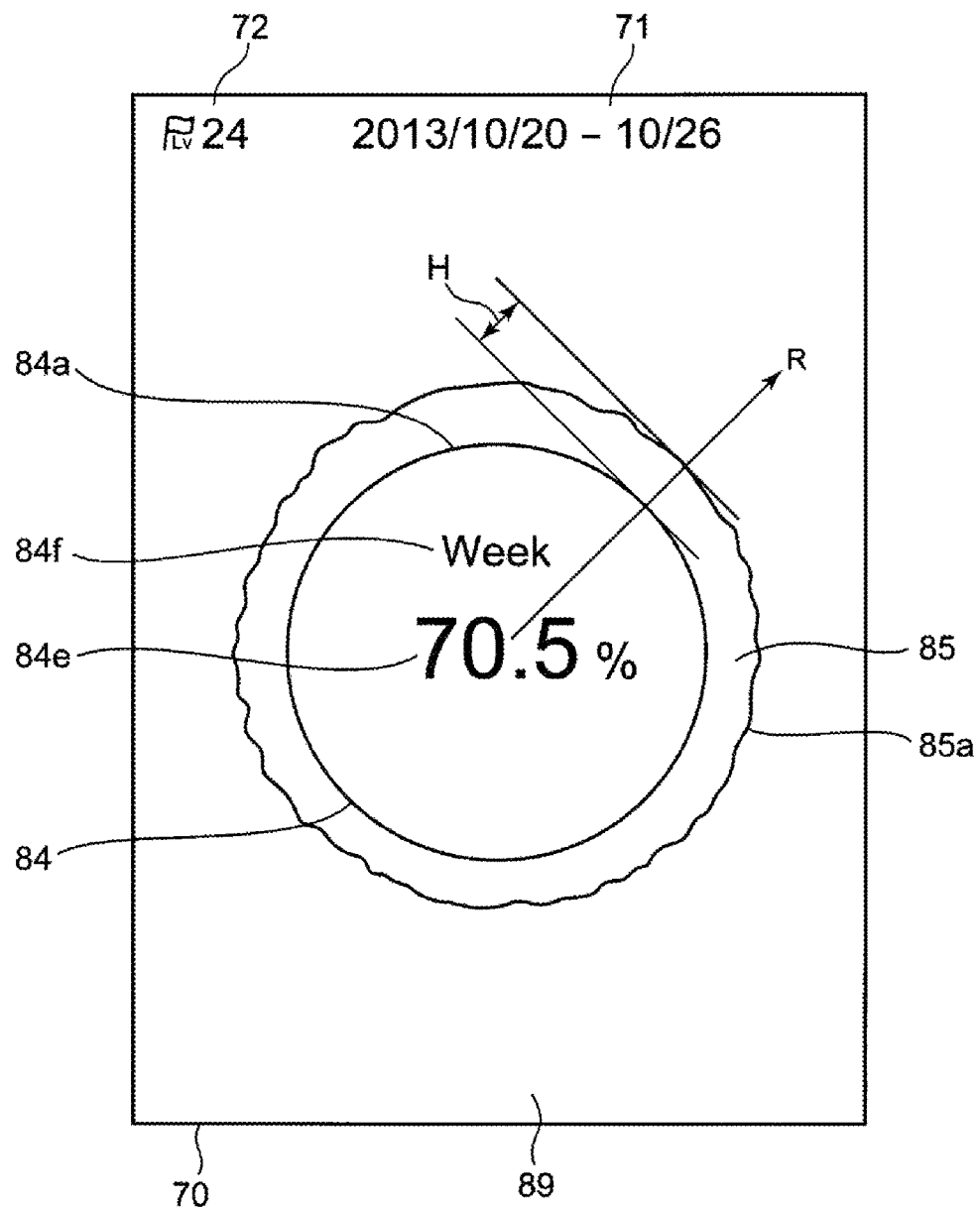
FIG. 10 is a diagram for schematically describing FIGS. 8A, 8B, 9A, and 9B.

With this image, as shown schematically in FIG. 10, the dates of the week that are the target of display (in this example, 2013/10/20 to 10/26 (Oct. 20, 2013 to Oct. 26, 2013) are written in the date field 71 in the upper center of the display screen 70, on the selected candidate image. Also, display indicating the one-week activity amount target value (in this example, 24 Ex) is written in the active level field 72 on the upper left side of the display screen 70. Also, the value of the one-week activity amount achievement degree (70.5% in the example shown in FIG. 10) is written in units of % in the central portion 84e of the circle 84. Also, a character string "Week" indicating that the period that is the target of display (target period) is a week is written in the portion 84f between the upper end portion 84a and the central portion 84e of the circle 84.

In the case where the image is displayed on the display screen 70 as described above, if the activity amount achievement degree for a certain week is small, for example, the radial direction dimension H of the ring-shaped region 85 will be smaller. If the activity amount achievement degree for another week is large, the radial direction dimension H of the ring-shaped region 85 will be larger. Moreover, the brightness of the ring-shaped region 85 gradually decreases moving outward in the radial direction so as to be continuous with the brightness of the background region 89. Also, the radial direction dimension H of the ring-shaped region 85 has fluctuations 85a around the circle 84. Accordingly, the ring-shaped region 85 displayed on the display screen 70 looks like a solar corona. That is, if the activity amount achievement degree is small as a result of the measurement subject 90 performing weak exercise for a certain week, it will look like a sun is burning dimly. If the activity amount achievement degree is large as a result of the measurement subject 90 performing vigorous exercise for another week, it will look like a sun is burning brightly. The intensity with which the sun burns suggests to the user the degree of energy expenditure due to exercise of the measurement subject 90. Accordingly, the user can intuitively know the activity amount achievement degree of the measurement subject 90. Also, because the one-week activity amount achievement degree is displayed as a numerical value in the central portion 84e of the circle 84, the user can know the exact activity amount achievement degree of the measurement subject 90.

In the above example, the activity amount target value in the active level field 72 was set by the user performing input thereof via the operation unit 230 to the memory 220 of the smartphone 200 in advance. However, there is no limitation to this, and the control unit 210 may function as the target value setting unit to acquire an achieved value for the activity amount of the measurement subject 90 for a past week prior to the above-described week (e.g., the previous week), and set the target value for the current week based on that achieved value. For example, if the achieved value for the activity amount of the measurement subject 90 is 28 Ex for the previous week, the target value for the current week may be set to 28 Ex, which is equal to the achieved value for the previous week. Also, the activity amount target value may be set to a target value larger than the achieved value, such as the achieved value 28 Ex+10% (about 31 Ex), so that the measurement subject 90 performs more vigorous exercise. In such a case, the user can intuitively know the achievement degree for the current week with respect to the activity amount target value based on the achieved value for the previous week by looking at the ring-shaped region 85 displayed on the display screen 70. Also, by looking at the numerical value in the central portion 84e of the circle 84, the user can know the exact achievement degree for the current week with respect to the activity amount target value based on the achieved value for the previous week.

In the second display example, the target period that was the target of display was one week, but there is no limitation to this. The target period may be, for example, one day, one month, or one year. A past period serving as a reference for setting the target value may also be, for example, one day, one month, or one year. Moreover, the length of the target period and the length of the past period may be different. In such a case, the target value for the target period may be calculated according to the length of the target period by converting the achieved value for the past period using the number of days.

Also, in the second display example, the achievement degree with respect to the activity amount target value was displayed as the information relating to the activity amount, but there is no limitation to this. As the information relating to the activity amount, an achievement degree with respect to a target value for exercise intensity or expended calories may be displayed like a solar corona. In such a case, the target values for the exercise intensity and the expended calories are stored in advance via the operation unit 230 in the memory 220 of the smartphone 200.

Also, in the second display example, the achievement degree with respect to the activity amount-related target value was calculated by the smartphone 200, but there is no limitation to this. The activity meter 100 may calculate the achievement degree with respect to the activity amount-related target value and transmit the information indicating the calculated achievement degree to the smartphone 200. In such a case, the target values for the exercise intensity, activity amount, and expended calories are stored in the memory 120 of the activity meter 100.

Also, in this embodiment, the activity meter 100 and the smartphone 200 mutually communicated by means of BLE communication, but there is no limitation to this. For example, the activity meter 100 and the smartphone 100 may communicate by means of NFC (Near Field Communication) when the smartphone 200 and the activity meter 100 are near each other.

Moreover, in this embodiment, the activity amount-related information display apparatus of the present invention was configured as a system including the activity meter 100 and the smartphone 200, but there is no limitation to this.

For example, the activity amount-related information display apparatus of the present invention may be constituted by only the smartphone 200. In such a case, it is assumed that the smartphone 200 includes an acceleration sensor. Also, the application software stored in the memory 220 of the smartphone 200 includes programs for calculating the exercise intensity, activity amount, and expended calories for each unit time in the control unit 210, and programs for calculating the achievement degree with respect to the target values for those values in the control unit 210. This makes it possible to form a small-sized and compact activity amount-related information display apparatus according to the present invention.

The above-described embodiment is merely an example and can be modified in various ways without departing from the scope of the invention.

The invention claimed is:

1. An activity amount-related information display apparatus for displaying information relating to an activity amount of a measurement subject as a graph on a display screen, comprising:
    a controller configured or programmed to define and function as:
        a value information acquirer that acquires value information indicating an exercise intensity, an activity amount, or expended calories of the measurement subject; and
        a first display processor that, on the display screen, sets a circle or a circular arc corresponding to one day, sets time divisions each indicating elapse of a unit time in the one day clockwise around the circle or the circular arc, and displays the value information as a graph composed of a collection of bars that extend outward in a radial direction around the circle or the circular arc and have lengths of a plurality of levels, the lengths each corresponding to a value indicated by the value information for a unit time; wherein
    on the display screen, the first display processor grays out a graph for a previous day, uses it as a background graph, and displays a graph for a current day written over the background graph using a color different from gray of the background graph.

2. The activity amount-related information display apparatus according to claim 1, wherein the controller is further configured or programmed to define and function as:
    a target value setter that acquires an achieved value for exercise intensity, activity amount, or expended calories of the measurement subject for a past period prior to the one day that serves as a target period, and based on the achieved value, sets a target value for exercise intensity, activity amount, or expended calories for the one day of the measurement subject;

an achievement degree acquirer that, based on the value information, calculates and acquires an achievement degree with respect to the target value for the exercise intensity, activity amount, or expended calories of the measurement subject for the one day; and a digital display processor that displays the achievement degree as a numerical value on the display screen.

3. An activity amount-related information display apparatus for displaying information relating to an activity amount of a measurement subject as a graph on a display screen, comprising:

a controller configured or programmed to define and function as:

an achievement degree acquirer that acquires an achievement degree with respect to a target value for exercise intensity, activity amount, or expended calories over a certain target period of the measurement subject; and a second display processor that, on the display screen, sets a dark-colored circle, a white or daylight-colored ring-shaped region surrounding the circle in a ring shape, and a dark-colored background region surrounding the ring-shaped region, and displays the ring-shaped region with a radial direction dimension varied according to the achievement degree, wherein a brightness of the ring-shaped region gradually decreases moving outward in a radial direction so as to be continuous with the brightness of the background region.

4. The activity amount-related information display apparatus according to claim 3, further comprising:

an image memory that stores a plurality of candidate images each having a different radial direction dimension, with which the ring-shaped region is to be displayed and; wherein the controller is further configured or programmed to define and function as an image selector that, among the plurality of candidate images, selects a candidate image having a radial direction dimension corresponding to the achievement degree for the target period.

5. The activity amount-related information display apparatus according to claim 3, wherein the controller is further configured or programmed to define and function as:

a target value setter that acquires an achieved value for exercise intensity, activity amount, or expended calories of the measurement subject for a past period prior to the target period, and based on the achieved value, sets the target value for the target period of the measurement subject.

6. The activity amount-related information display apparatus according to claim 1, wherein the first display processor makes the length of the bar longer as the value indicated by the value information becomes larger.

7. The activity amount-related information display apparatus according to claim 6, wherein the first display processor makes the length of the bar longer by increasing a number of colored segments in the bar.

* * * * *